United States Patent
Wrenn et al.

(10) Patent No.: US 9,384,192 B2
(45) Date of Patent: Jul. 5, 2016

(54) SYSTEMS AND METHODS FOR TRACKING A SLIDE USING A COMPOSITE BARCODE LABEL

(71) Applicant: LEICA BIOSYSTEMS IMAGING, INC., Vista, CA (US)

(72) Inventors: Mark Wrenn, Vista, CA (US); Dirk Soenksen, Vista, CA (US)

(73) Assignee: LEICA BIOSYSTEMS IMAGING, INC., Vista, CA (US)

( * ) Notice: Subject to any disclaimer, the term of this patent is extended or adjusted under 35 U.S.C. 154(b) by 0 days.

(21) Appl. No.: 14/417,005

(22) PCT Filed: Mar. 15, 2013

(86) PCT No.: PCT/US2013/032328
§ 371 (c)(1),
(2) Date: Jan. 23, 2015

(87) PCT Pub. No.: WO2014/018114
PCT Pub. Date: Jan. 30, 2014

(65) Prior Publication Data
US 2015/0169555 A1 Jun. 18, 2015

Related U.S. Application Data

(60) Provisional application No. 61/675,741, filed on Jul. 25, 2012.

(51) Int. Cl.
*G06K 7/10* (2006.01)
*G06F 17/30* (2006.01)
(Continued)

(52) U.S. Cl.
CPC .............. *G06F 17/30* (2013.01); *G06Q 10/10* (2013.01); *G06Q 50/22* (2013.01);
(Continued)

(58) Field of Classification Search
CPC ............... G06F 17/30; H04N 1/32133; H04N 2201/323; H04N 2201/3269; H04N 2201/3271
USPC ........ 235/375, 462.01, 462.07, 462.09, 462.1
See application file for complete search history.

(56) References Cited

U.S. PATENT DOCUMENTS 6,805,294 B2 * 10/2004 Itoh .................. G01N 35/00732
235/462.01
7,207,481 B2 4/2007 Barenburg et al.
(Continued)

FOREIGN PATENT DOCUMENTS

| JP | 2001-133464 A | 5/2001 |
| JP | 2010-145420 A | 7/2010 |
| WO | 2014018114 A1 | 1/2014 |

OTHER PUBLICATIONS

International Search Report and Written Opinion for related International Application No. PCT/US2013/032328 mailed Jun. 26, 2013, in 10 pages.

(Continued)

*Primary Examiner* — Paultep Savusdiphol
(74) *Attorney, Agent, or Firm* — Procopio, Cory, Hargreaves & Savitch LLP; Pattric J. Rawlins

(57) ABSTRACT

Systems and methods for tracking a slide comprising a tissue sample. In an embodiment, data is received from a Laboratory Information System (LIS) barcode associated with a slide and a proprietary barcode generated by a slide staining system, such as a Ventana slide staining system, to track the slide through the staining process. A new label is printed that contains both the LIS barcode and the proprietary barcode, and is attached to the slide. When the slide is subsequently scanned by a slide scanning system, the slide scanning system reads and decodes the LIS barcode to obtain a LIS barcode value. The LIS barcode value may then be used to retrieve information associated with the slide.

15 Claims, 5 Drawing Sheets

(51) Int. Cl.
*H04N 1/32* (2006.01)
*G06Q 10/10* (2012.01)
*G06Q 50/22* (2012.01)

(52) U.S. Cl.
CPC ..... *H04N 1/32133* (2013.01); *H04N 2201/323* (2013.01); *H04N 2201/3269* (2013.01); *H04N 2201/3271* (2013.01)

(56) References Cited

U.S. PATENT DOCUMENTS

| | | | | |
|---|---|---|---|---|
| 9,150,983 | B1* | 10/2015 | Astle | C40B 60/14 |
| 2003/0100043 | A1* | 5/2003 | Kalra | G01N 1/312 435/40.5 |
| 2004/0011871 | A1* | 1/2004 | Harper | G06K 7/10851 235/462.01 |
| 2004/0084531 | A1* | 5/2004 | Itoh | G01N 35/00732 235/462.01 |
| 2004/0219069 | A1* | 11/2004 | Kalra | G01N 1/312 422/400 |
| 2005/0061878 | A1* | 3/2005 | Barenburg | G06K 7/1434 235/385 |
| 2006/0029519 | A1* | 2/2006 | Nakaya | G01N 1/312 422/63 |
| 2007/0131772 | A1 | 6/2007 | Lubow | |
| 2007/0145142 | A1* | 6/2007 | Lubow | G06K 1/121 235/462.01 |
| 2009/0234671 | A1* | 9/2009 | Jones | G06F 19/366 705/2 |
| 2010/0044429 | A1* | 2/2010 | Orkin | G06F 19/366 235/375 |
| 2010/0167334 | A1* | 7/2010 | Williamson, IV | G06F 19/366 435/29 |
| 2010/0178695 | A1* | 7/2010 | Nakaya | G01N 1/312 435/309.1 |
| 2011/0114719 | A1* | 5/2011 | Graupner | B01L 3/545 235/375 |
| 2012/0267440 | A1* | 10/2012 | Nakaya | G01N 1/312 235/494 |
| 2014/0022631 | A1* | 1/2014 | Hunnell | G02B 21/34 359/396 |

OTHER PUBLICATIONS

International Preliminary Report on Patentability for related International Application No. PCT/US2013/032328 mailed Feb. 5, 2015, in 7 pages.

* cited by examiner

Decoded: 025522

Decoded: SX08-12345;S123;coz

SYSTEMS AND METHODS FOR TRACKING A SLIDE USING A COMPOSITE BARCODE LABEL

PRIORITY

This application is a National Stage filing under 35 U.S.C. §371 of International Application PCT/US13/032328 filed on Mar. 13, 2013 which claims priority to U.S. Provisional Patent App. No. 61/675,741, filed on Jul. 25, 2012. The entirety of each application is hereby incorporated herein by reference.

FIELD OF THE INVENTION

The systems and methods disclosed herein relate generally to the tracking of pathology slides, and more particularly, to tracking pathology slides which are associated with two different barcodes for two different systems.

BACKGROUND

Some conventional automated slide stainers, such as those produced by Ventana Medical Systems, Inc., and sold under the trademark Ventana, require proprietary barcodes to automate the process of staining tissue samples. For example, Ventana™ systems generate a label, comprising a one-dimensional barcode, which is physically placed on a slide containing a tissue sample. In this manner, the staining system is able to identify and manage the slide during automated staining. The Ventana™ barcode encodes a number which is only meaningful to Ventana™ systems.

Typically, prior to staining and the application of the Ventana™ barcode label, a first barcode label has already been placed on the slide. This first barcode label is usually associated with the source of the tissue sample (e.g., a patient). It may be a Laboratory Information System (LIS) barcode, generated by a histology or other laboratory and placed on the slide to maintain an association of the slide with its source for tracking purposes. LIS barcodes are generally two-dimensional or matrix barcodes (e.g., a Quick Response (QR) code).

In practice, at least in part due to limited space on the slide, the Ventana™ barcode label is physically placed over the LIS barcode label, thereby obscuring the LIS barcode label. Once the LIS barcode is obscured, it is unable to be read and tracked by systems which must process the slide following application of the Ventana™ barcode label (e.g., following the Ventana™ staining process). For instance, after a tissue sample on a slide has been stained, the slide is often digitized by a scanning system.

Ventana™ maintains tight confidentiality as to the meaning of the number embedded in its proprietary barcode. Thus, in practice, if a histology laboratory desires to use a digital pathology scanning system other than a Ventana™ scanning system, it must peel the Ventana™ barcode label off of the slide and/or re-label the slide in order to restore the ability to track the slide using the LIS barcode. In some cases, the information must be manually written on the slide. In either case, such a situation introduces workflow inefficiencies and opportunities for errors to occur.

SUMMARY

Therefore, one objective of the present disclosure is to eliminate this need to peel off labels or re-enter data following a staining process requiring a proprietary barcode label, while maintaining the ability to track a slide throughout a digital pathology scanning process using data from an LIS barcode. Embodiments disclosed herein improve reliability and accuracy, and allow non-proprietary equipment to automatically retrieve LIS data.

Accordingly, a method for tracking a slide is disclosed. In an embodiment, the method comprises, by at least one hardware processor, receiving Laboratory Information System (LIS) data from a first LIS barcode, receiving proprietary data from a first proprietary barcode, and generating a composite barcode label comprising a second LIS barcode and a second proprietary barcode, wherein the second LIS barcode comprises the LIS data and the second proprietary barcode comprises the proprietary data; and by a digital pathology slide scanning system, scanning the second LIS barcode while scanning a slide, decoding the second LIS barcode to obtain the LIS data, and retrieving information from at least one database based on the LIS data.

Furthermore, a system for tracking a slide is disclosed. In an embodiment, the system comprises at least one hardware processor that receives Laboratory Information System (LIS) data decoded from a first LIS barcode, receives proprietary data decoded from a first proprietary barcode, and generates a composite barcode label comprising a second LIS barcode and a second proprietary barcode, wherein the second LIS barcode comprises the LIS data and the second proprietary barcode comprises the proprietary data; and a digital pathology slide scanning system that scans the second LIS barcode while scanning a slide, decodes the second LIS barcode to obtain the LIS data, and retrieves information from at least one database based on the LIS data.

BRIEF DESCRIPTION OF THE DRAWINGS

The details of the present invention, both as to its structure and operation, may be gleaned in part by study of the accompanying drawings, in which like reference numerals refer to like parts, and in which.

DETAILED DESCRIPTION

Figure 1:
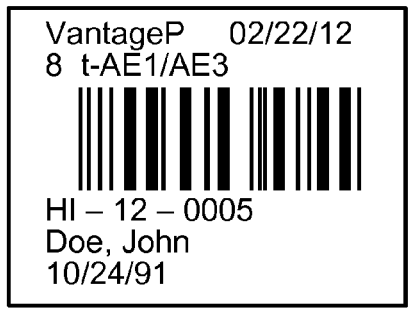
FIG. 1 illustrates an example proprietary barcode, according to an embodiment.
Figure 2:
FIG. 2 illustrates an example LIS barcode, according to an embodiment.

Barcodes comprise encoded or embedded data. A barcode reader scans and translates the barcode into the embedded data. This data may comprise, for example, a string of alphanumeric or other characters. In the case of an LIS barcode illustrated in FIG. 1, the embedded data may comprise a string of letters, numbers, and/or other characters (e.g., "SX08-12345;S123;coz"). In the case of a Ventana™ barcode, illustrated in FIG. 2, the embedded data comprises a string of numbers (e.g., "025522"). While embodiments are discussed herein with reference to Ventana™ stainers or barcodes, it should be understood that the disclosed systems and methods are not limited to a specific brand of stainer or barcode. Rather, the disclosed systems and methods may be used with any brand of stainer and barcode, as well as other types of systems and encodings.

Data Collection.

According to an embodiment, a barcode reader is provided at the time that the proprietary barcode label (e.g., Ventana™ barcode) would normally be applied to a slide (e.g., by overlaying it on an LIS barcode label already adhered to the slide). For example, the barcode reader may be provided next to a proprietary barcode printer. The barcode reader may comprise any conventional barcode reading system. For instance, it may comprise a wand which reads barcodes using a laser. Alternatively, the barcode reader may comprise an imaging device, or an application residing on a device comprising an imaging device, which captures an image of the barcode, for example, using a camera or other optical viewing device. Barcode readers are well-known in the art, and even ubiquitous on consumer devices, such as mobile phones and tablets. The particular implementation of barcode reading is not essential to the disclosed embodiments, and will not be discussed herein in detail.

When a slide arrives at a staining station, which may comprise a Ventana™ or other staining system, it is typically already labeled with an LIS barcode. A technician enters data into the Ventana™ or other proprietary software to generate a Ventana™ or other proprietary barcode. At this point, prior to application of the proprietary barcode, both the LIS and proprietary barcodes are available and accessible to the technician. Thus, according to an embodiment, the technician uses the barcode reader to read both the LIS and proprietary barcodes, either serially or simultaneously.

The barcode reader may be communicatively connected to a software application, e.g., via one or more application programming interfaces (APIs). The application receives the embedded data of each of the LIS and proprietary barcodes from the barcode reader. The application may generate a user interface to be displayed on a display device, such as a computer monitor. For instance, the application may reside on a computer system, comprising a central processing unit ("CPU"), memory, and a display. The computer may also have network access, including access to one or more databases. The computer system may further comprise or be interfaced with a barcode wand or imaging device, and may execute a barcode reading or translating application. The computer may also comprise or be interfaced with a barcode label printer. The computer or application may be installed in proximity to the proprietary stainer or barcode printer.

The application may prompt a technician, via the user interface, to indicate which barcode is the LIS barcode and which is the Ventana or other proprietary barcode. Alternatively, the application may be able to automatically determine which barcode is which. For example, since the LIS barcode and proprietary barcode may utilize different formats (e.g., two-dimensional v. one-dimensional) or contain embedded data in different formats (e.g., different lengths, allowable characters, patterns, and the like), the application may be able to differentiate the two types of barcodes without user intervention. The application may store or access preset rules for differentiating the two types of barcodes. These rules may be configurable or selectable by an operator of the system.

Figure 4:
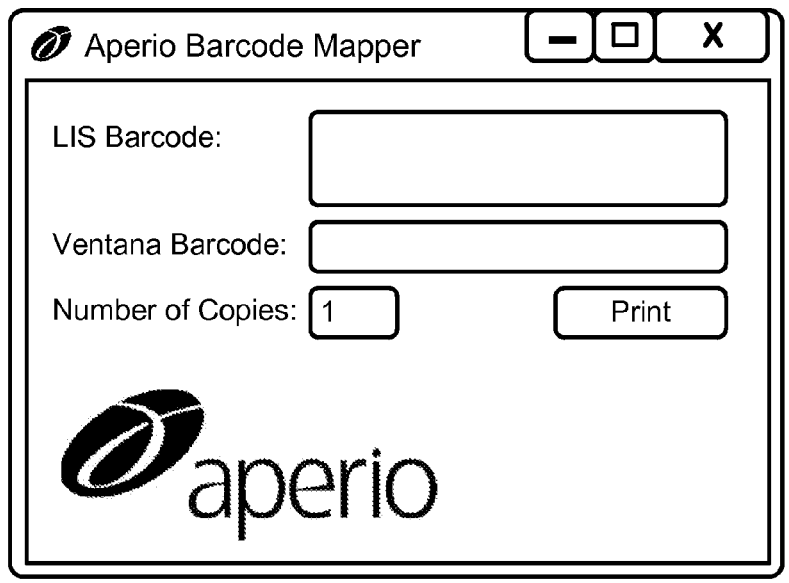
FIG. 4 illustrates an example user interface for printing a composite barcode label, according to an embodiment.

FIG. 4 illustrates an example user interface, according to an embodiment. The user interface may place a cursor next to (or otherwise place the focus on) a box associated with the LIS barcode, or otherwise indicate that the user is to scan the LIS barcode. The user (e.g., histo-tech) can then scan the LIS barcode using a barcode wand or other barcode reader, and the user interface may display the value of the scanned LIS barcode in the box. After scanning the LIS barcode, the user interface may place a cursor next to (or otherwise place the focus on) a box associated with the proprietary barcode, or otherwise indicate that the user is to scan the proprietary barcode. Alternatively, the user interface may wait until the user selects an input (e.g., box) or otherwise indicates that he or she is ready to scan the proprietary barcode. The user can then scan the proprietary barcode using the barcode reader, and the user interface may display the value of the scanned proprietary barcode in the box. In an embodiment, the user may also specify the number of copies of a label to print.

Label Printing.

The application receives the data embedded in the two barcodes (e.g., from a barcode reading application), and generates corresponding barcodes for printing. The generated barcodes may be identical or different in format and/or encoding from the original, scanned barcodes. Alternatively, the application may receive a digital image of the scanned barcodes, and print these digital images on the composite label, without ever having to decode the barcodes.

In response to a user interaction (e.g., pressing of a "print" button on the user interface), the application may initiate printing of a composite barcode label (or the specified number of composite barcode labels in embodiments which allow printing of multiple copies of the label). The application may interface with a barcode label printer and initiate printing by sending the images or data to be printed to the printer.

Figure 3:
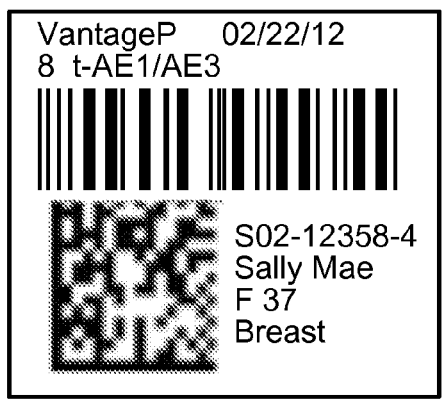
FIG. 3 illustrates an example composite barcode label, according to an embodiment.

As demonstrated in FIG. 3, the composite barcode label may comprise two barcodes. One barcode will comprise an encoding of the data from the LIS barcode. The other barcode will comprise an encoding of the data from the proprietary barcode.

Data Lookup.

According to an embodiment, when a slide arrives at a digital pathology scanning station, which may comprise an Aperio® ScanScope® slide scanner or other scanner, the scanner can scan the LIS barcode on the composite barcode label. The LIS barcode may be scanned either as the scanner scans the sample (e.g., tissue sample) on the slide, or separately before or after scanning the sample on the slide. A barcode reading module or application, which may be stored on a memory of the digital pathology slide scanner, can then extract the data embedded in the LIS barcode. For example, the module may decode the LIS barcode resulting in a character string.

The digital pathology slide scanner may have network access to one or more databases. Thus, a barcode reading module or another module or application residing on a memory of the digital pathology slide scanner and executed by a processor of the slide scanner can query the one or more databases via at least one network to which the slide scanner is connected. For example, the module may query the databases via one or more networks using the data decoded from the LIS barcode as a key. In this manner, the LIS barcode data can be used to retrieve further information about the slide. For example, this information may be retrieved from an LIS database storing a plurality of data associated with the value encoded in the LIS barcode. The data may comprise information about a patient associated with (e.g., comprising the source of) the slide sample. Alternatively or additionally, the data may comprise any other information which may be usefully associated with a slide.

Example Embodiment.

Figure 5:
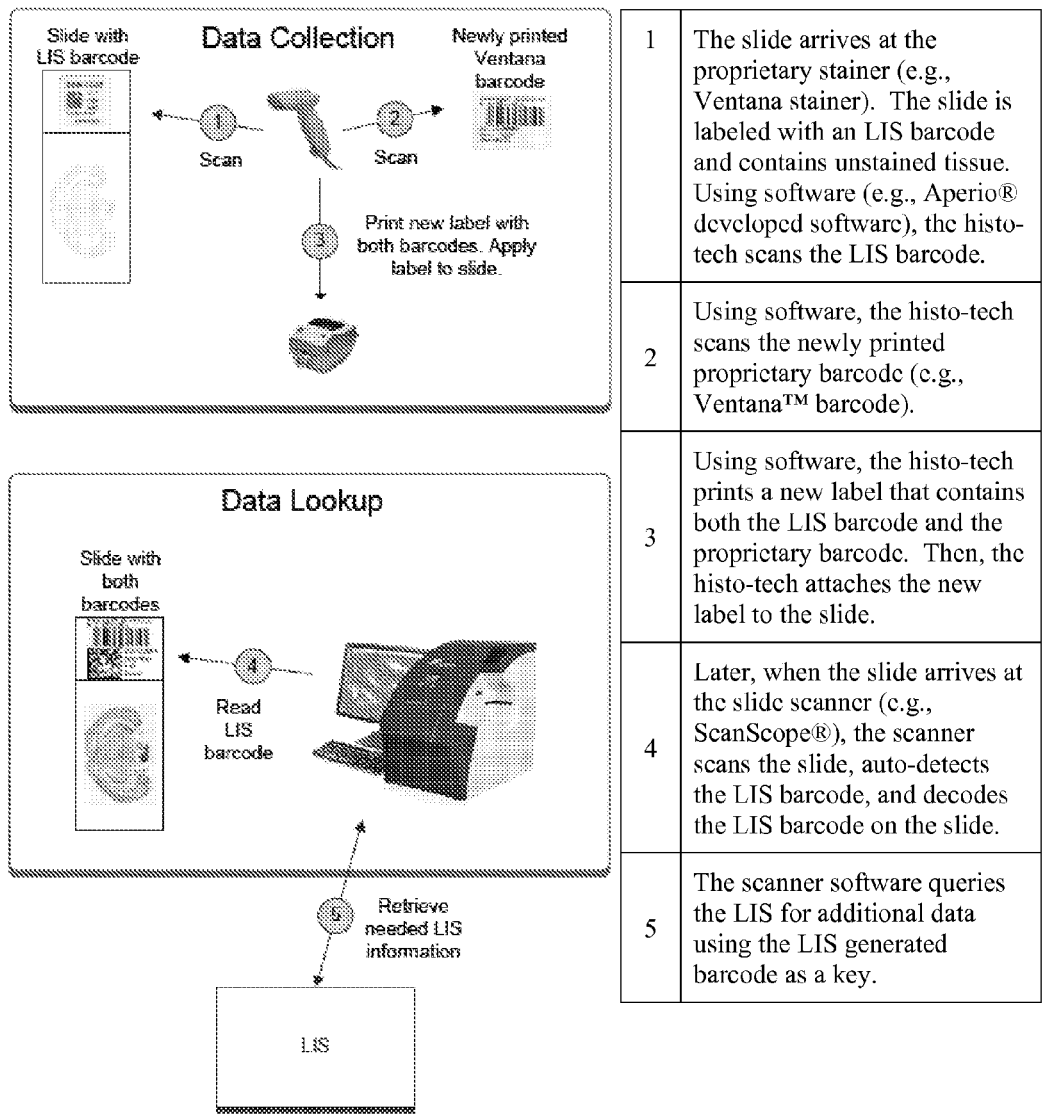
FIG. 5 illustrates a flow diagram for an example process of data collection and data lookup, according to an embodiment.

FIG. 5 illustrates a process of data collection and lookup, according to an embodiment. A slide comprising an unstained sample and labeled with an LIS barcode is brought to a staining station. In step 1, the LIS barcode is scanned using a barcode wand or other barcode reader attached to a computer system. For instance, the barcode wand may be operated by a histo-technician or other user. The value of the LIS barcode is decoded and stored in a memory (e.g., Random Access Memory, non-volatile memory, etc.) on the computer system, or alternatively, the digital image of the barcode is stored in the memory. At some point, a proprietary barcode (e.g., Ventana™ barcode) is generated to be used with the slide (e.g., by a slide stainer). In step 2, the Ventana™ barcode is scanned using the barcode wand. The value of the Ventana™ barcode is decoded and stored in a memory of the computer system, or alternatively, the digital image of the barcode is stored in the memory.

In step 3, the histo-technician prints a new composite barcode label that contains both the LIS barcode and the proprietary barcode, and attaches the composite barcode label to the slide. The slide is stained or otherwise processed by a Ventana™ or other proprietary system using the proprietary barcode on the composite barcode label. Then the slide is brought to a digital pathology scanning station to be digitized.

In step 4, at the scanning station, the LIS barcode is read. For instance, the LIS barcode may be digitized by a digital pathology slide scanning system along with the sample on the slide, and then decoded by a barcode reading module of the slide scanning system.

In step 5, the value obtained by the digital pathology slide scanning system from the LIS barcode is sent as a parameter in a request or query to a server storing LIS information. In response to the query, the server may use the LIS value as a key to retrieve associated LIS information. The server may then return the LIS information, which may comprise patient data or other information, to the slide scanner. Additionally, the digital slide image that results from scanning the slide may also be associated with the LIS barcode or the LIS information.

Example Slide Scanning Systems.

Figure 6:
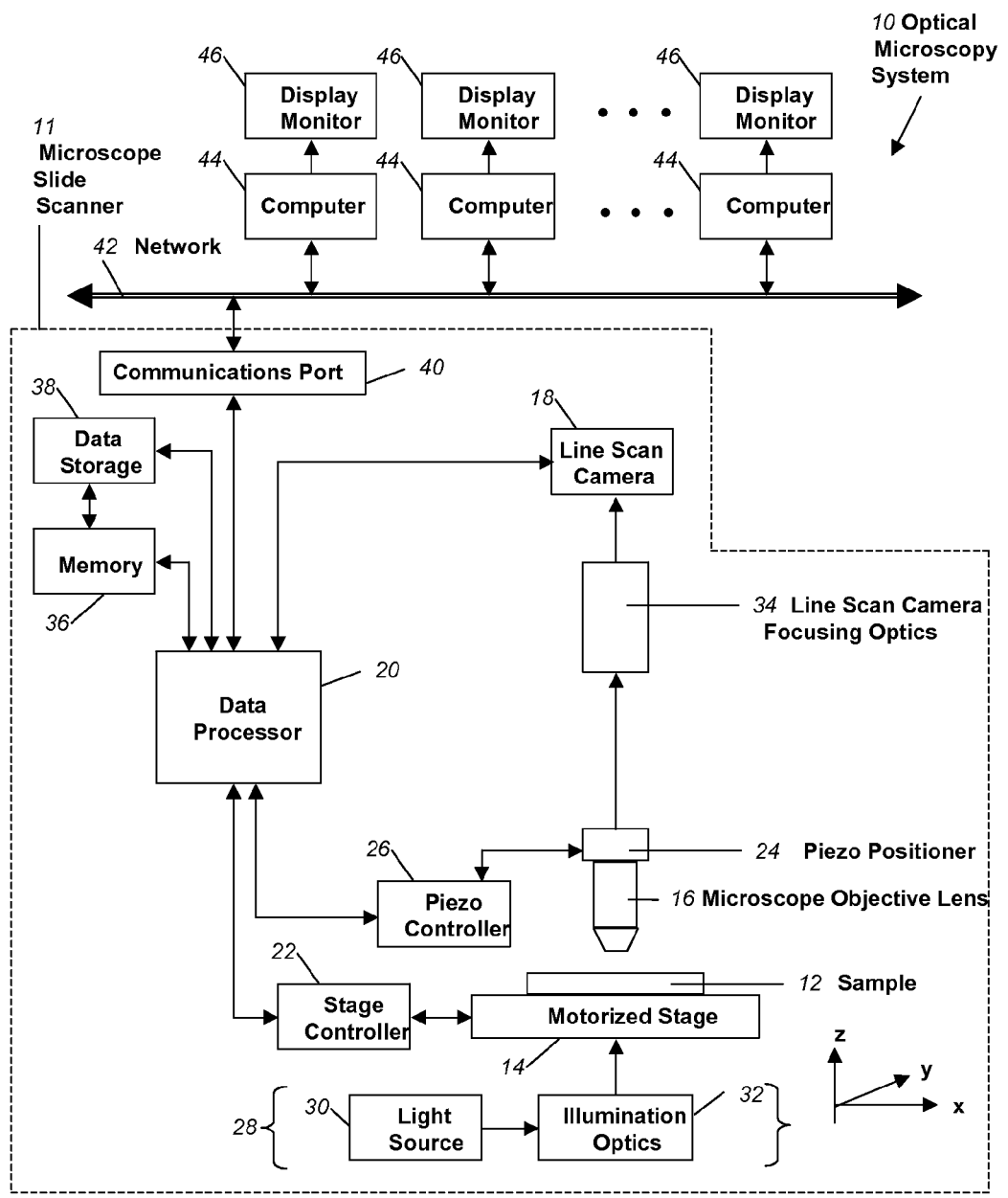
FIG. 6 illustrate a microscope slide scanner, according to an embodiment.

FIG. 6 illustrates an example of a digital pathology slide scanner 11 which can be used as the disclosed digital pathology scanner. A primary imaging sensor and the focusing sensor(s) may be arranged (e.g., in conjunction with a beam-splitter) as line scan camera 18. The imaging sensor and focusing sensor(s) can receive image information from a sample 12 through the microscope objective lens 16 and/or the focusing optics 34. Furthermore, they can provide information to, and/or receive information from, data processor 20. Data processor 20 is communicatively connected to memory 36 and data storage 38. Data processor 20 may further be communicatively connected to a communications port, which may be connected by at least one network 42 to one or more computers 44, which may in turn be connected to display monitor(s) 46.

Data processor 20 may also be communicatively connected to and provide instructions to a stage controller 22, which controls a motorized stage 14 of the digital pathology slide scanner 11. The motorized stage 14 supports sample 12 and moves in one or more directions in the X-Y plane. Data processor 20 may also be communicatively connected to and provide instructions to a piezo controller 26, which controls a piezo positioner 24. The piezo positioner 24 is configured to move the objective lens 16 in the Z direction. The digital pathology slide scanner 11 also comprises a light source 30 and/or illumination optics 32 to illuminate the sample 12, either from above or below.

Figure 7:
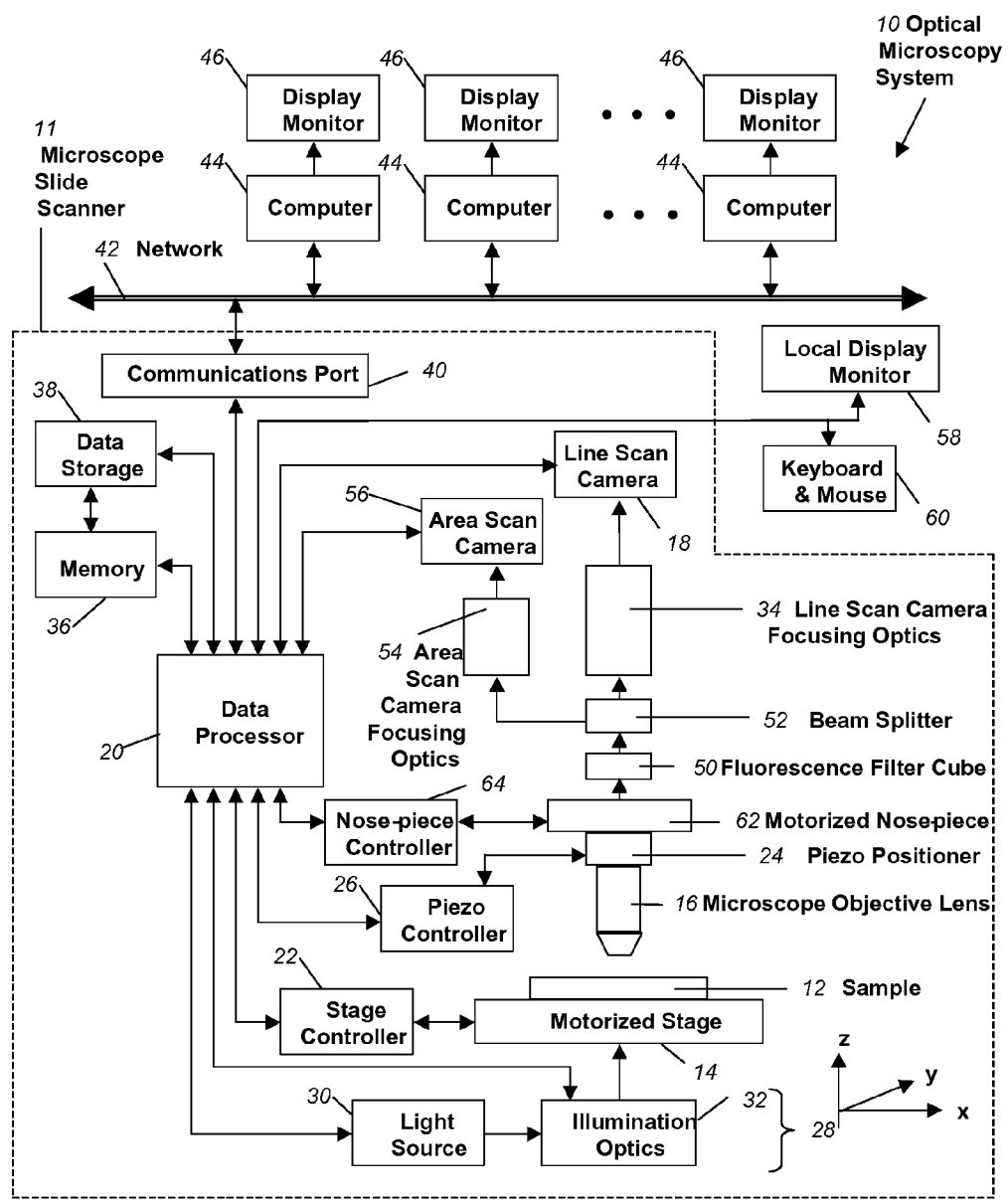
FIG. 7 illustrate a microscope slide scanner, according to an embodiment.

FIG. 7 illustrates a further embodiment of the digital pathology slide scanner 11 from FIG. 6. The digital pathology scanner 11 may comprise an area scan camera 56, in addition to the line scan camera 18 (which comprises the imaging sensor and focusing sensor(s) as described above). The area scan camera 56 may receive image information through the area scan camera focusing optics 54, and may be configured to communicate with data processor 20. A beam-splitter 52 may be inserted along the optical axis of the objective lens 16 to split the image beam into separate paths to both the line scan camera 18 and the area scan camera 56.

The digital pathology scanner 11 may also comprise additional elements, such as fluorescence filter cube 50 and/or a motorized nosepiece 62. The motorized nosepiece 62 may be controlled by a nosepiece controller 64, and the nosepiece controller 64 may communicate with data processor 20. In addition, the data processor 20 may be communicatively connected with and control light source 30 and/or illumination optics 32. In an embodiment, the digital pathology scanner 11 may further comprise a local display monitor 58 and input device 60 (e.g., keyboard and/or mouse).

Figure 8:
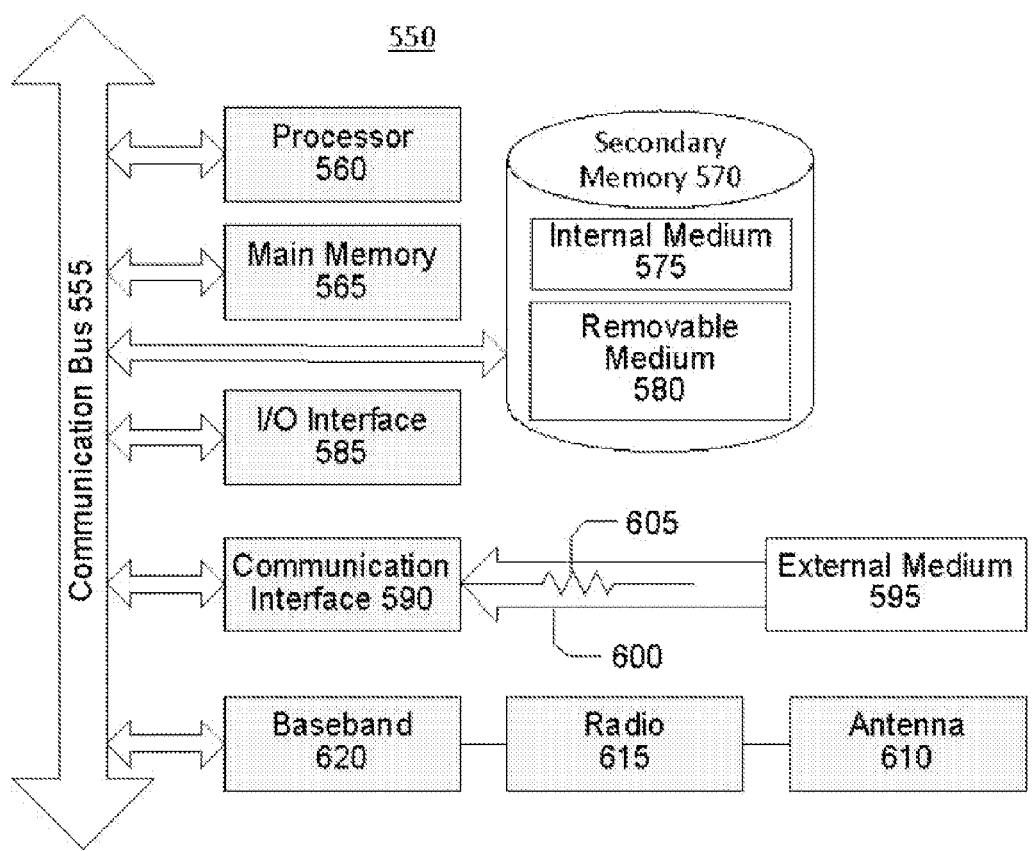
FIG. 8 is a block diagram illustrating an example computer system that may be used in connection with various embodiments described herein.

FIG. 8 is a block diagram illustrating an example wired or wireless system 550 that may be used in connection with various embodiments described herein. For example, system 550 may be used as or in conjunction with one or more of the mechanisms or processes described above, and may represent components of a barcode wand or other barcode reader, digital pathology scanner 11, and/or other devices described herein. The system 550 can be a server or any conventional personal computer, or any other processor-enabled device that is capable of wired or wireless data communication. Other computer systems and/or architectures may be also used, as will be clear to those skilled in the art.

The system 550 preferably includes one or more processors, such as processor 560. Additional processors may be provided, such as an auxiliary processor to manage input/output, an auxiliary processor to perform floating point mathematical operations, a special-purpose microprocessor having an architecture suitable for fast execution of signal processing algorithms (e.g., digital signal processor), a slave processor subordinate to the main processing system (e.g., back-end processor), an additional microprocessor or controller for dual or multiple processor systems, or a coprocessor. Such auxiliary processors may be discrete processors or may be integrated with the processor 560. Examples of processors which may be used with system 550 include, without limitation, the Pentium® processor, Core i7® processor, and Xeon® processor, all of which are available from Intel Corporation of Santa Clara, Calif.

The processor 560 is preferably connected to a communication bus 555. The communication bus 555 may include a data channel for facilitating information transfer between storage and other peripheral components of the system 550. The communication bus 555 further may provide a set of signals used for communication with the processor 560, including a data bus, address bus, and control bus (not shown). The communication bus 555 may comprise any standard or non-standard bus architecture such as, for example, bus architectures compliant with industry standard architecture (ISA), extended industry standard architecture (EISA), Micro Channel Architecture (MCA), peripheral component interconnect (PCI) local bus, or standards promulgated by the Institute of Electrical and Electronics Engineers (IEEE) including IEEE 488 general-purpose interface bus (GPIB), IEEE 696/S-100, and the like.

System 550 preferably includes a main memory 565 and may also include a secondary memory 570. The main memory 565 provides storage of instructions and data for programs executing on the processor 560, such as one or more of the functions and/or modules discussed above. It should be understood that programs stored in the memory and executed by processor 560 may be written and/or compiled according to any suitable language, including without limitation C/C++, Java, JavaScript, Perl, Visual Basic, .NET, and the like. The main memory 565 is typically semiconductor-based memory such as dynamic random access memory (DRAM) and/or static random access memory (SRAM). Other semiconductor-based memory types include, for example, synchronous dynamic random access memory (SDRAM), Rambus dynamic random access memory (RDRAM), ferroelectric random access memory (FRAM), and the like, including read only memory (ROM).

The secondary memory 570 may optionally include an internal memory 575 and/or a removable medium 580, for example a floppy disk drive, a magnetic tape drive, a compact disc (CD) drive, a digital versatile disc (DVD) drive, other optical drive, a flash memory drive, etc. The removable medium 580 is read from and/or written to in a well-known manner. Removable storage medium 580 may be, for example, a floppy disk, magnetic tape, CD, DVD, SD card, etc.

The removable storage medium 580 is a non-transitory computer-readable medium having stored thereon computer executable code (i.e., software) and/or data. The computer software or data stored on the removable storage medium 580 is read into the system 550 for execution by the processor 560.

In alternative embodiments, secondary memory 570 may include other similar means for allowing computer programs or other data or instructions to be loaded into the system 550. Such means may include, for example, an external storage medium 595 and an interface 590. Examples of external storage medium 595 may include an external hard disk drive or an external optical drive, or and external magneto-optical drive.

Other examples of secondary memory 570 may include semiconductor-based memory such as programmable read-only memory (PROM), erasable programmable read-only memory (EPROM), electrically erasable read-only memory (EEPROM), or flash memory (block oriented memory similar to EEPROM). Also included are any other removable storage media 580 and communication interface 590, which allow software and data to be transferred from an external medium 595 to the system 550.

System 550 may include a communication interface 590. The communication interface 590 allows software and data to be transferred between system 550 and external devices (e.g. printers), networks, or information sources. For example, computer software or executable code may be transferred to system 550 from a network server via communication interface 590. Examples of communication interface 590 include a built-in network adapter, network interface card (NIC), Personal Computer Memory Card International Association (PCMCIA) network card, card bus network adapter, wireless network adapter, Universal Serial Bus (USB) network adapter, modem, a network interface card (NIC), a wireless data card, a communications port, an infrared interface, an IEEE 1394 fire-wire, or any other device capable of interfacing system 550 with a network or another computing device.

Communication interface 590 preferably implements industry promulgated protocol standards, such as Ethernet IEEE 802 standards, Fiber Channel, digital subscriber line (DSL), asynchronous digital subscriber line (ADSL), frame relay, asynchronous transfer mode (ATM), integrated digital services network (ISDN), personal communications services (PCS), transmission control protocol/Internet protocol (TCP/IP), serial line Internet protocol/point to point protocol (SLIP/PPP), and so on, but may also implement customized or non-standard interface protocols as well.

Software and data transferred via communication interface 590 are generally in the form of electrical communication signals 605. These signals 605 are preferably provided to communication interface 590 via a communication channel 600. In one embodiment, the communication channel 600 may be a wired or wireless network, or any variety of other communication links. Communication channel 600 carries signals 605 and can be implemented using a variety of wired or wireless communication means including wire or cable, fiber optics, conventional phone line, cellular phone link, wireless data communication link, radio frequency ("RF") link, or infrared link, just to name a few.

Computer executable code (i.e., computer programs or software) is stored in the main memory 565 and/or the secondary memory 570. Computer programs can also be received via communication interface 590 and stored in the main memory 565 and/or the secondary memory 570. Such computer programs, when executed, enable the system 550 to perform the various functions of the present invention as previously described.

In this description, the term "computer readable medium" is used to refer to any non-transitory computer readable storage media used to provide computer executable code (e.g., software and computer programs) to the system 550. Examples of these media include main memory 565, secondary memory 570 (including internal memory 575, removable medium 580, and external storage medium 595), and any peripheral device communicatively coupled with communication interface 590 (including a network information server or other network device). These non-transitory computer readable mediums are means for providing executable code, programming instructions, and software to the system 550.

In an embodiment that is implemented using software, the software may be stored on a computer readable medium and loaded into the system 550 by way of removable medium 580, I/O interface 585, or communication interface 590. In such an embodiment, the software is loaded into the system 550 in the form of electrical communication signals 605. The software, when executed by the processor 560, preferably causes the processor 560 to perform the inventive features and functions previously described herein.

In an embodiment, I/O interface 585 provides an interface between one or more components of system 550 and one or more input and/or output devices. Example input devices include, without limitation, keyboards, touch screens or other touch-sensitive devices, biometric sensing devices, computer mice, trackballs, pen-based pointing devices, and the like. Examples of output devices include, without limitation, cathode ray tubes (CRTs), plasma displays, light-emitting diode (LED) displays, liquid crystal displays (LCDs), printers, vacuum florescent displays (VFDs), surface-conduction electron-emitter displays (SEDs), field emission displays (FEDs), and the like.

The system 550 also includes optional wireless communication components that facilitate wireless communication over a voice and over a data network. The wireless communication components comprise an antenna system 610, a radio system 615 and a baseband system 620. In the system 550, radio frequency (RF) signals are transmitted and received over the air by the antenna system 610 under the management of the radio system 615.

In one embodiment, the antenna system 610 may comprise one or more antennae and one or more multiplexors (not shown) that perform a switching function to provide the antenna system 610 with transmit and receive signal paths. In the receive path, received RF signals can be coupled from a multiplexor to a low noise amplifier (not shown) that amplifies the received RF signal and sends the amplified signal to the radio system 615.

In alternative embodiments, the radio system 615 may comprise one or more radios that are configured to communicate over various frequencies. In one embodiment, the radio system 615 may combine a demodulator (not shown) and modulator (not shown) in one integrated circuit (IC). The demodulator and modulator can also be separate components. In the incoming path, the demodulator strips away the RF carrier signal leaving a baseband receive audio signal, which is sent from the radio system 615 to the baseband system 620.

If the received signal contains audio information, then baseband system 620 decodes the signal and converts it to an analog signal. Then the signal is amplified and sent to a speaker. The baseband system 620 also receives analog audio signals from a microphone. These analog audio signals are converted to digital signals and encoded by the baseband system 620. The baseband system 620 also codes the digital signals for transmission and generates a baseband transmit audio signal that is routed to the modulator portion of the radio system 615. The modulator mixes the baseband transmit audio signal with an RF carrier signal generating an RF transmit signal that is routed to the antenna system and may pass through a power amplifier (not shown). The power amplifier amplifies the RF transmit signal and routes it to the antenna system 610 where the signal is switched to the antenna port for transmission.

The baseband system 620 is also communicatively coupled with the processor 560. The central processing unit 560 has access to data storage areas 565 and 570. The central processing unit 560 is preferably configured to execute instructions (i.e., computer programs or software) that can be stored in the memory 565 or the secondary memory 570. Computer programs can also be received from the baseband processor 610 and stored in the data storage area 565 or in secondary memory 570, or executed upon receipt. Such computer programs, when executed, enable the system 550 to perform the various functions of the present invention as previously described. For example, data storage areas 565 may include various software modules (not shown).

Various embodiments may also be implemented primarily in hardware using, for example, components such as application specific integrated circuits (ASICs), or field programmable gate arrays (FPGAs). Implementation of a hardware state machine capable of performing the functions described herein will also be apparent to those skilled in the relevant art. Various embodiments may also be implemented using a combination of both hardware and software.

Furthermore, those of skill in the art will appreciate that the various illustrative logical blocks, modules, circuits, and method steps described in connection with the above described figures and the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block, circuit or step is for ease of description. Specific functions or steps can be moved from one module, block or circuit to another without departing from the invention.

Moreover, the various illustrative logical blocks, modules, functions, and methods described in connection with the embodiments disclosed herein can be implemented or performed with a general purpose processor, a digital signal processor (DSP), an ASIC, FPGA, or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such that the processor can read information from, and write information to, the storage medium. In the alternative, the storage medium can be integral to the processor. The processor and the storage medium can also reside in an ASIC.

Any of the software components described herein may take a variety of forms. For example, a component may be a stand-alone software package, or it may be a software package incorporated as a "tool" in a larger software product. It may be downloadable from a network, for example, a website, as a stand-alone product or as an add-in package for installation in an existing software application. It may also be available as a client-server software application, as a web-enabled software application, and/or as a mobile application.

The above description of the disclosed embodiments is provided to enable any person skilled in the art to make or use the invention. Various modifications to these embodiments will be readily apparent to those skilled in the art, and the general principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

What is claimed is:

1. A method for tracking a slide, the method comprising:
by at least one hardware processor,
receiving Laboratory Information System (LIS) data from a first LIS barcode, receiving proprietary data from a first proprietary barcode, and generating a composite barcode label comprising a second LIS barcode and a second proprietary barcode, wherein the second LIS barcode comprises the LIS data and the second proprietary barcode comprises the proprietary data, and wherein the second LIS barcode is not identical to the first LIS barcode; and by a slide scanning system, scanning the second LIS barcode while scanning a slide, decoding the second LIS barcode to obtain the LIS data, and retrieving information from at least one database based on the LIS data.

2. The method of claim 1, wherein the first proprietary barcode is a barcode generated by a slide staining system.

3. The method of claim 1, wherein the first LIS barcode is a two-dimensional barcode, and the first proprietary barcode is a one-dimensional barcode.

4. The method of claim 1, wherein the second proprietary barcode is identical to the first proprietary barcode.

5. The method of claim 1, wherein retrieving information from at least one database based on the LIS data comprises:

sending a request comprising the LIS data over at least one network to at least one server comprising the at least one database; and receiving a response comprising the information over the at least one network from the at least one server.

6. The method of claim 1, wherein scanning the LIS barcode while scanning a slide comprises acquiring an image of the LIS barcode while it is affixed to the slide.

7. The method of claim 1, further comprising, by the at least one hardware processor, providing a user interface which prompts a user to scan the first LIS barcode and the first proprietary barcode.

8. A system for tracking a slide, the system comprising:

at least one hardware processor that receives Laboratory Information System (LIS) data decoded from a first LIS barcode, receives proprietary data decoded from a first proprietary barcode, and generates a composite barcode label comprising a second LIS barcode and a second proprietary barcode, wherein the second LIS barcode comprises the LIS data and the second proprietary barcode comprises the proprietary data, and wherein the second LIS barcode is not identical to the first LIS barcode; and a slide scanning system that scans the second LIS barcode while scanning a slide, decodes the second LIS barcode to obtain the LIS data, and retrieves information from at least one database based on the LIS data.

9. The system of claim 8, wherein the first proprietary barcode is a barcode generated by a slide staining system.

10. The system of claim 9, wherein the slide staining system is a slide staining system sold by Ventana Medical Systems.

11. The system of claim 8, wherein the first LIS barcode is a two-dimensional barcode, and the first proprietary barcode is a one-dimensional barcode.

12. The system of claim 8, wherein the second proprietary barcode is identical to the first proprietary barcode.

13. The system of claim 8, wherein retrieving information from at least one database based on the LIS data comprises:

sending a request comprising the LIS data over at least one network to at least one server comprising the at least one database; and receiving a response comprising the information over the at least one network from the at least one server.

14. The system of claim 8, wherein scanning the LIS barcode while scanning a slide comprises acquiring an image of the LIS barcode while it is affixed to the slide.

15. The system of claim 8, wherein the at least one hardware processor also provides a user interface which prompts a user to scan the first LIS barcode and the first proprietary barcode.

* * * * *